(12) United States Patent
Craven et al.

(10) Patent No.: US 7,599,058 B2
(45) Date of Patent: Oct. 6, 2009

(54) METHODS FOR PLASMA DIAGNOSTICS AND THE MEASUREMENT OF THIN FILMS

(75) Inventors: David Craven, Palo Alto, CA (US); Ryan Roberts, Scotts Valley, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 11/963,974

(22) Filed: Dec. 24, 2007

(65) Prior Publication Data

US 2008/0158557 A1    Jul. 3, 2008

Related U.S. Application Data

(62) Division of application No. 11/016,155, filed on Dec. 17, 2004, now abandoned.

(51) Int. Cl.
*G01J 3/30* (2006.01)
(52) U.S. Cl. ................. 356/316; 356/317; 356/326; 356/72

(58) Field of Classification Search ............. 356/316, 356/317, 326, 72; 250/226, 216, 227.23, 250/227.17, 230
See application file for complete search history.

(56) References Cited

U.S. PATENT DOCUMENTS 6,677,604 B2 *    1/2004   Mitrovic ............. 250/573

* cited by examiner

*Primary Examiner*—L. G Lauchman
(74) *Attorney, Agent, or Firm*—Martine Penilla & Gencarella, LLP.

(57) ABSTRACT

Methods for obtaining and analyzing data from a spectral source is provided. The method includes identifying an environment that is capable of generating spectral information, and obtaining the generated spectral information from the environment. The method further includes splitting the generated spectral information into a plurality of spectral data units. The spectral data units are further captured in separate storage entities and separately processed in parallel in order to produce a complete processing and quantification of the environment.

17 Claims, 13 Drawing Sheets

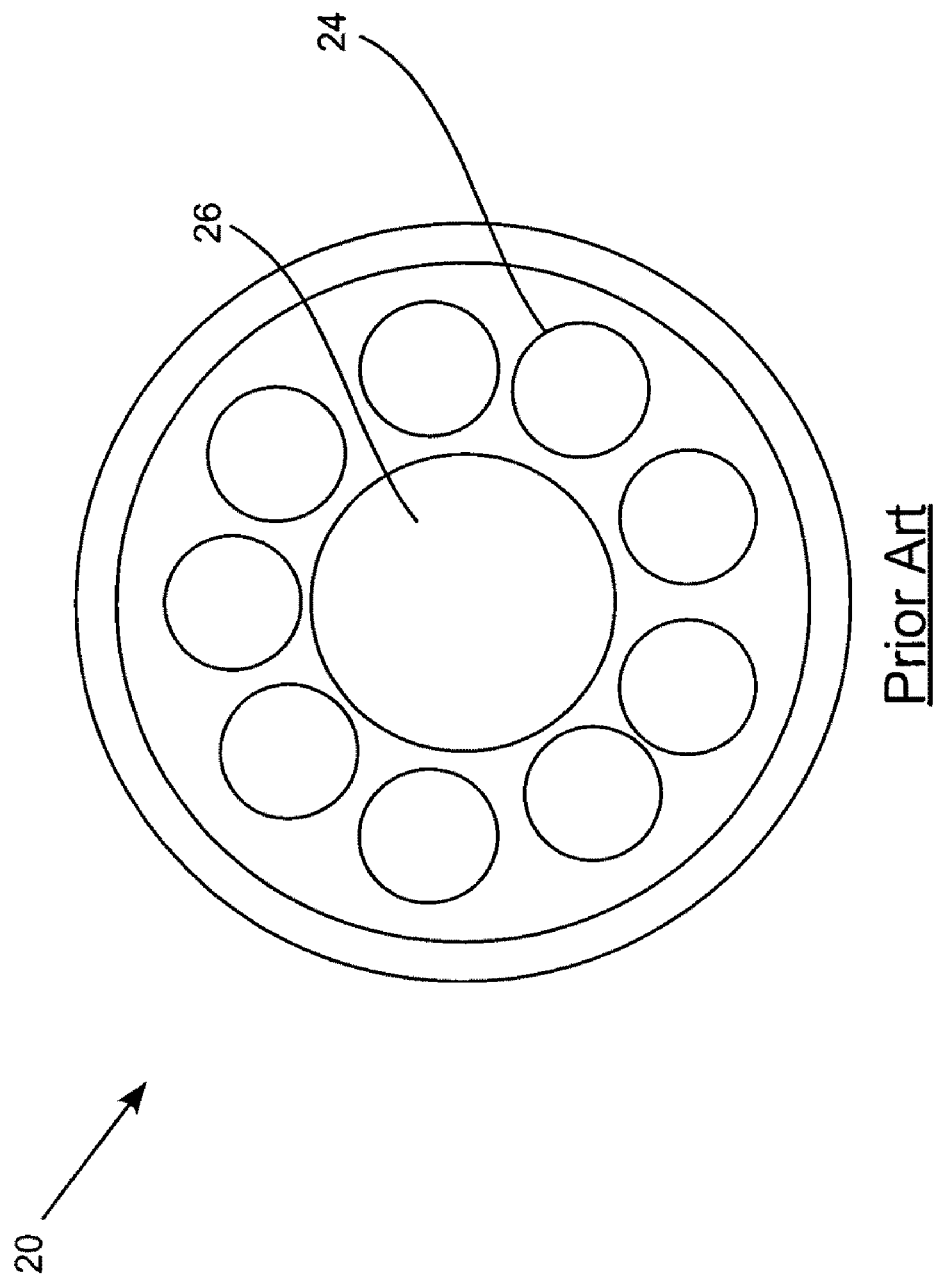
Fig. 1a — Prior Art

| | 429.3 | 432.1 | 435.0 | 437.8 | 440.6 | 443.5 | 446.3 | 449.1 | 452.0 | 454.8 | 457.6 |
|---|---|---|---|---|---|---|---|---|---|---|---|
| 17 | 18834.14 | 16738.31 | 15261.66 | 14040.89 | 12662.54 | 12087.37 | 11391.86 | 11078.54 | 10875.31 | 10849.74 | 10828.37 |
| 17.5 | 18811.52 | 16691.77 | 15227.49 | 14006.54 | 12631.69 | 12056.74 | 11375.91 | 11061.66 | 10865.11 | 10848.49 | 10833.63 |
| 18 | 18764.17 | 16662.89 | 15183.77 | 13975.31 | 12619.09 | 12046.6 | 11368.86 | 11056.49 | 10870.63 | 10852.2 | 10832.71 |
| 18.5 | 18724.94 | 16602.86 | 15129.37 | 13915.74 | 12569.03 | 12003.83 | 11340.06 | 11032.46 | 10846.23 | 10835.03 | 10816.23 |
| 19 | 18665.26 | 16556.8 | 15078.4 | 13886.29 | 12536.29 | 11985.11 | 11310.66 | 11020.03 | 10840.63 | 10831.66 | 10813 |
| 19.5 | 18607.86 | 16486.83 | 15027.66 | 13835.37 | 12494.6 | 11952.26 | 11303.51 | 11010.03 | 10817.66 | 10818.23 | 10809.74 |
| 20 | 18553.91 | 16433.57 | 14976.34 | 13792.31 | 12453.26 | 11926.69 | 11272.23 | 10996.97 | 10819.06 | 10816 | 10802.54 |
| 20.5 | 18500.23 | 16378.66 | 14924.72 | 13750.8 | 12428 | 11899.09 | 11259.91 | 10989.72 | 10819.31 | 10813.77 | 10809.89 |
| 21 | 18423.63 | 16314.52 | 14877.51 | 13693.11 | 12397.26 | 11873.6 | 11248.34 | 10977.8 | 10806.4 | 10809.46 | 10810.52 |
| 21.5 | 18368.29 | 16259.06 | 14824.31 | 13659.6 | 12368.43 | 11851.23 | 11239.29 | 10972.06 | 10804.63 | 10802.23 | 10811.72 |
| 22 | 18303.77 | 16211.72 | 14788.97 | 13632.31 | 12349.31 | 11849.17 | 11240.26 | 10991.94 | 10822.49 | 10816.91 | 10815.11 |
| 22.5 | 18244 | 16146.69 | 14738.54 | 13596.31 | 12330.89 | 11835.52 | 11240.03 | 10984.31 | 10826.09 | 10825.43 | 10825.31 |
| 23 | 18190.86 | 16102.46 | 14696.86 | 13558.89 | 12308.83 | 11827.6 | 11227.31 | 10989.71 | 10824.37 | 10841.4 | 10830.66 |
| 23.5 | 18110.49 | 16041.66 | 14650.06 | 13515.06 | 12287.14 | 11819.97 | 11225.26 | 10996.11 | 10838.03 | 10828.14 | 10842.23 |
| 24 | 18049.49 | 15992.63 | 14615.43 | 13492.43 | 12279.37 | 11816.46 | 11235.06 | 11000.57 | 10851.94 | 10849.69 | 10856.17 |
| 24.5 | 17989.2 | 15947.2 | 14585.8 | 13482.94 | 12265.54 | 11811.94 | 11252.34 | 11020.8 | 10862.09 | 10865 | 10858.6 |
| 25 | 17924.46 | 15899.31 | 14543.49 | 13469.83 | 12276.49 | 11822.37 | 11248.03 | 11021.52 | 10880.91 | 10870.03 | 10852.6 |
| 25.5 | 17879.29 | 15867.63 | 14521.17 | 13453.54 | 12266.43 | 11829.03 | 11256.57 | 11030.72 | 10881.63 | 10890.89 | 10872.77 |
| 26 | 17819.54 | 15837.52 | 14495.57 | 13446.54 | 12270.94 | 11838.97 | 11277.29 | 11053 | 10897.66 | 10894.94 | 10882.43 |
| 26.5 | 17771.97 | 15810.8 | 14496.77 | 13445.06 | 12272.72 | 11862.14 | 11291.71 | 11061.43 | 10903.89 | 10904.34 | 10893.4 |
| 27 | 17732.6 | 15785.29 | 14482 | 13439.4 | 12288.77 | 11866.94 | 11313 | 11092 | 10936.91 | 10924.77 | 10910.06 |
| 27.5 | 17699.31 | 15746.94 | 14469.97 | 13448.09 | 12305.14 | 11885.77 | 11322.63 | 11093.66 | 10936.09 | 10922.94 | 10916.69 |
| 28 | 17669.72 | 15741.03 | 14463.77 | 13451.57 | 12323.34 | 11901.52 | 11344.06 | 11114.57 | 10955.66 | 10942.46 | 10927.34 |
| 28.5 | 17642.31 | 15731.69 | 14460.14 | 13470.29 | 12343.86 | 11930.06 | 11369.91 | 11136.29 | 10961.6 | 10957.06 | 10933.31 |
| 29 | 17617.34 | 15717.29 | 14468.83 | 13470.09 | 12362.54 | 11938.06 | 11373.86 | 11154.31 | 10968.34 | 10948.74 | 10929.37 |
| 29.5 | 17592.51 | 15721.29 | 14477.34 | 13492.89 | 12383.09 | 11970.31 | 11408.46 | 11169.54 | 10983.06 | 10970.09 | 10933.97 |
| 30 | 17586.91 | 15724.14 | 14487.14 | 13501.86 | 12404.71 | 11993.72 | 11433.74 | 11179.11 | 11003.17 | 10967.8 | 10946.06 |
| 30.5 | 17589.54 | 15736.52 | 14512.66 | 13544.89 | 12439.63 | 12029.09 | 11453.11 | 11211.71 | 11012.77 | 10985.89 | 10947.74 |

Fig. 8b

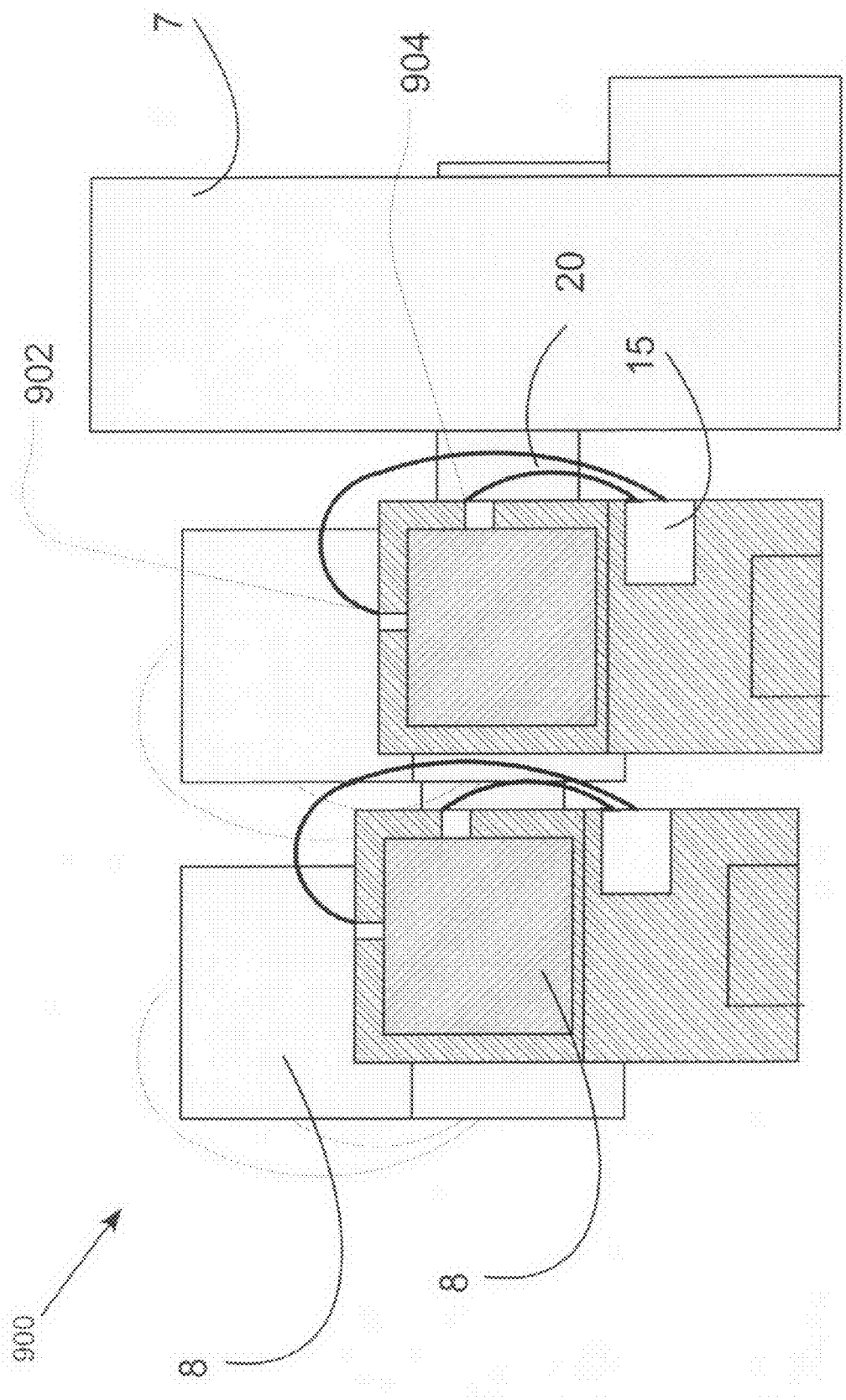
Fig. 9b (Side View)

METHODS FOR PLASMA DIAGNOSTICS AND THE MEASUREMENT OF THIN FILMS

CLAIM OF PRIORITY

This application is a divisional application of U.S. application Ser. No. 11/016,155, filed on Dec. 17, 2004, now abandoned and entitled "Method and Apparatus for Plasma Diagnostics and the Measurement of Thin Films", which is herein incorporated by reference.

CROSS REFERENCE TO RELATED APPLICATIONS

This application is related to U.S. patent application Ser. No. 10/810,209, entitled "METHOD AND APPARATUS FOR MEASUREMENT OF THIN FILMS AND RESIDUES ON SEMICONDUCTOR SUBSTRATES," filed on Mar. 26, 2003. The disclosure of this patent application is incorporated herein by reference.

BACKGROUND OF THE INVENTION

1. Field of the Invention

The invention relates generally to semiconductor fabrication and more specifically to measurement of films and plasma emissions during wafer processing.

2. Description of the Related Art

In the fabrication of semiconductor devices, there is a need to measure material features on substrates. Typically, integrated circuit devices are manufactured in the form of multi-level structures. At the substrate level, transistor devices having p-type and n-type doped regions are formed. In subsequent levels, interconnect metallization lines are patterned and electrically connected to the transistor devices to define the desired functional device. Dielectric materials, such as silicon dioxide, insulate patterned conductive features. Etching paths through these layers provides a means for interconnecting contacting semiconductor devices such as transistors. Metallization line patterns are formed in dielectric materials, and then metal CMP operations are performed to remove excess metallization.

During integrated circuit fabrication there are many opportunities for gathering metrology data, that is measuring material and device properties on substrates. Many properties can be determined by capturing a signal indicating the device, feature or material. As features and the thickness of films employed in the manufacture of semiconductors continue to decrease in size, the task of collecting metrology becomes more sophisticated and precise. Properties of materials on the substrate are carefully monitored throughout the fabrication process, but the task is more difficult during interlayer dielectric (ILD) stages, that is, when stacks consist of multiple dielectric and metal film layers.

This disclosure relates to the measurement of thin films through the use of standard optical methods utilizing reflections off and transmission through materials and characterization of plasma or chemical emissions during material processing. Optical emission spectroscopy (OES), interferometry, spectral-reflectomety, ellipsometry and other suitable methods employ the use of and characterization of wavelengths of light and have been used extensively in the semiconductor arts. Optical sensors maybe used for non-contact thickness measurement of transparent films, such as silicon dioxide and other materials used in the manufacture of semiconductor devices in addition to classification of plasma emissions (optical emission spectroscopy) during plasma etch operations. In some operations, such as plasma etching, emissions during a process provide real-time monitoring and process control. Optical techniques such as ellipsometry and reflectometry have been used extensively in the semiconductor arts for measurement of thin films (U.S. Pat. No. 4,899,055 "Thin Film Thickness Measuring Method"). Lam Research has been a leader in providing in-situ classification and measurement of plasma etch processes (U.S. Pat. No. 6,160,621 "Method and Apparatus for In-Situ Monitoring of Plasma Etch and Deposition Processes Using a Pulsed Broadband Light Source").

Transmissive films include a broad range of dielectric and semi-conductive materials that allow certain wavelengths of light to pass through based on the index of refraction and extinction coefficient of the particular material. Illumination by a light source such as a xenon lamp provides wavelengths of light from ultraviolet to near infrared ranges. The selection of the light source may be dependent on the type of films to be measured by the optical sensor. The light source may be pulsed or flashed at defined periods to enable error subtraction (smoothing or averaging) in addition to cancellation of movement induced by the rotation of the substrate and scanning of a sensor. A computer in concert with a spectrograph (described below) can control operation of the strobe, including such parameters as the period of the flashing illumination.

A receiving element, such as a fiberoptic cable 20 shown in FIG. 1, is capable of collecting light returning from the surface of the substrate. The fiberoptic cable 20, may include a core 26 as well as a number of transmission lines 26 all capable of transmitting the light signal. The fiberoptic cable 20 passes the received light to a spectrograph for analysis. The spectrograph may be incorporated in the computer, or may be a standalone unit that serves as input into the computer. A spectrograph includes an arrangement of semiconductors elements that transform light energy into electrical energy such as a charge-coupled device array (CCD) or photo diodes and a method of extracting this position-dependent information.

When used to measure film thickness, the spectrograph utilizes interference of reflected light from a pair of surfaces to determination of the thickness of defined materials. Spectral reflectometry can be used to measure the difference in the optical path length between interfaces, to provide a measurement of the thickness of film layers.

Another technique utilizing linearly polarized light from an illumination source may be used to measure layer thickness. Linearly polarized light (transmitted via a fiberoptic cable) reflected off a thin film, becomes elliptically polarized. Analysis of this change across the spectrum (provided by a spectrometer described below) provides material properties of the film or stack of films such as the thickness and refractive index of the material.

Measurement systems utilizing spectral information, especially those that provide full surface mapping require a tremendous amount of processing power for complete collection, storage and analyzing of data retrieved by the sensors. The problem with known approaches is that the amount of data is necessarily limited by the speed of the associated computer or processor. As processor speeds continue to increase it will be possible to take more samples and reduce the integration time.

In optical emission spectroscopy (OES) plasma diagnostics, spectrographs may be employed in order to monitor and classify emission characteristics during a process such as etching layers of semiconductor material. During etch operations, known reactive gasses are excited and accelerated to the surface of a wafer by high frequency (RF) energy. At the wafer surface the chemicals added to the chamber react and in some cases recombine with material on the surface of the wafer. By-products (incl. recombinants) of the reaction are noticeable in the plasma discharge within the chamber before being pumped away by a vacuum system. A fiberoptic cable 20 positioned to capture the glow of the reaction transmits the signal back to the spectrograph for analysis. The plasma emissions associated with particular reactions (a.k.a. signatures) can be classified in a manner so that known good processes and known failures can later be classified during or immediately after processing operations. Precise plasma monitoring activities require relatively high sample rates and efficient processing which is taxing for many of today's commercially available systems.

The present invention provides a solution to the data collection bottleneck experienced while monitoring, analyzing, and classifying data obtained from in-situ and post-process film measurement, as well as in-situ plasma diagnostics during etch operations.

SUMMARY OF THE INVENTION

Broadly speaking, the present invention is a method of data collection and reduction for systems providing thin film measurement and plasma diagnostics (OES). It should be appreciated that the present invention can be implemented in numerous ways, including as an apparatus, a system, a device, or a method. Several inventive embodiments of the present invention are described below.

In accordance with one embodiment of the present invention, a method for obtaining data from spectral sources is provided. The method includes identifying an environment that is capable of generating spectral information, obtaining the generated spectral information from the environment, and splitting the generated spectral information into a plurality of spectral data units. The method further includes capturing each of the spectral data units in separate storage entities and separately processing groups of the plurality of spectral data units. The separate processing is combined to produce a complete processing of the plurality of spectral data units which defines a quantification of the environment.

In accordance with another embodiment of the present invention, an apparatus for obtaining data obtained from spectral sources is provided. The apparatus includes a distribution unit capable of being interconnected with a spectral source. The spectral source may include light reflected off or transmitted through of a wafer surface or emanating from plasma emissions within the spectral source. The distribution unit is capable of distributing the spectral source into discrete quantities. The apparatus further includes a plurality of distribution channels capable of transmitting discrete quantities of spectra from the distribution unit, an array of optical sensing devices, capable of receiving the discrete quantities of spectra and sensing properties of the light and a plurality of data processors capable of separately receiving the sensed properties by the array of optical sensing devices. The data processors separately process the sensed properties to establish quantification of the light within the spectral source.

In accordance with yet another embodiment of the present invention, a system for monitoring semiconductor processes is provided. The system includes a processing chamber capable of containing gaseous species, RF energy, and a material to be etched or deposited. The process chamber has ports adjacent to a reaction location contained therein. The ports are capable of receiving signals reflected from the material and capable receiving signals from plasma emissions above the material. The system includes transmission media capable of transmitting the signals from the processing chamber to a distribution unit. The distribution unit capable of splitting the signals reflected from the material or received from plasma emissions above the material into a plurality of spectral data units. Storage entities capable of capturing each of the spectral data units and a plurality of data processors capable of separately processing groups of the plurality of spectral data units are also included in the system. A complete processing of the plurality of spectral data units is provided by separate processors such that characteristics of the material in the process chamber are defined.

In another embodiment of the present invention a method of quantifying an environment is provided. The method includes a means for transmitting light from the environment to a distribution unit, a means for splitting light from environment into a plurality of spectral data units, a means for capturing each of the spectral data units; and means for separately processing groups of the plurality of spectral data units. The separate processing is configured to produce a complete processing of the plurality of spectral data units. The complete processing of the plurality of spectral data units defines characteristics of the material in the environment.

The advantages of the present invention are numerous. Facilitation of film measurement and in-situ plasma diagnostics through the use of parallel analysis and processing provides an efficient alternative to traditional means of acquiring process information. The present method improves the use of the above discussed technology by providing a technique for reducing the integration time associated with the obtaining and processing of signals from an illumination source off a wafer surface or from plasma emissions. By splitting the incoming optical signal to different arrays and processors, integration of one data point or sample is not necessarily limited by traditional backlogs in acquisition and processing time of the previous inspection point or data sample. Faster sample rates and efficient processing enhance the capabilities of processing and measurement equipment. It is to be understood that the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate exemplary embodiments of the invention and together with the description serve to explain the principles of the invention.

FIG. 1a is a cross-section of a fiberoptic cable.

FIG. 8b is a spreadsheet containing data for wavelengths across the visual spectrum, accordance with one embodiment of the present invention.

FIG. 9b is a side view diagram of a processing tool having several chambers complete with the spectral analysis system, in accordance with one embodiment of the present invention.

DETAILED DESCRIPTION OF THE INVENTION

This disclosure describes a method and apparatus for reducing processing times in plasma diagnostic tools and thin-film measurement tools. Several exemplary embodiments of the invention will now be described in detail with reference to the accompanying drawings. In the following description, numerous specific details are set forth in order to provide a thorough understanding of the present invention. It will be understood, however, to one skilled in the art, that the present invention may be practiced without some or all of these specific details. In other instances, well known process operations have not been described in detail in order not to unnecessarily obscure the present invention.

Figure 1B:
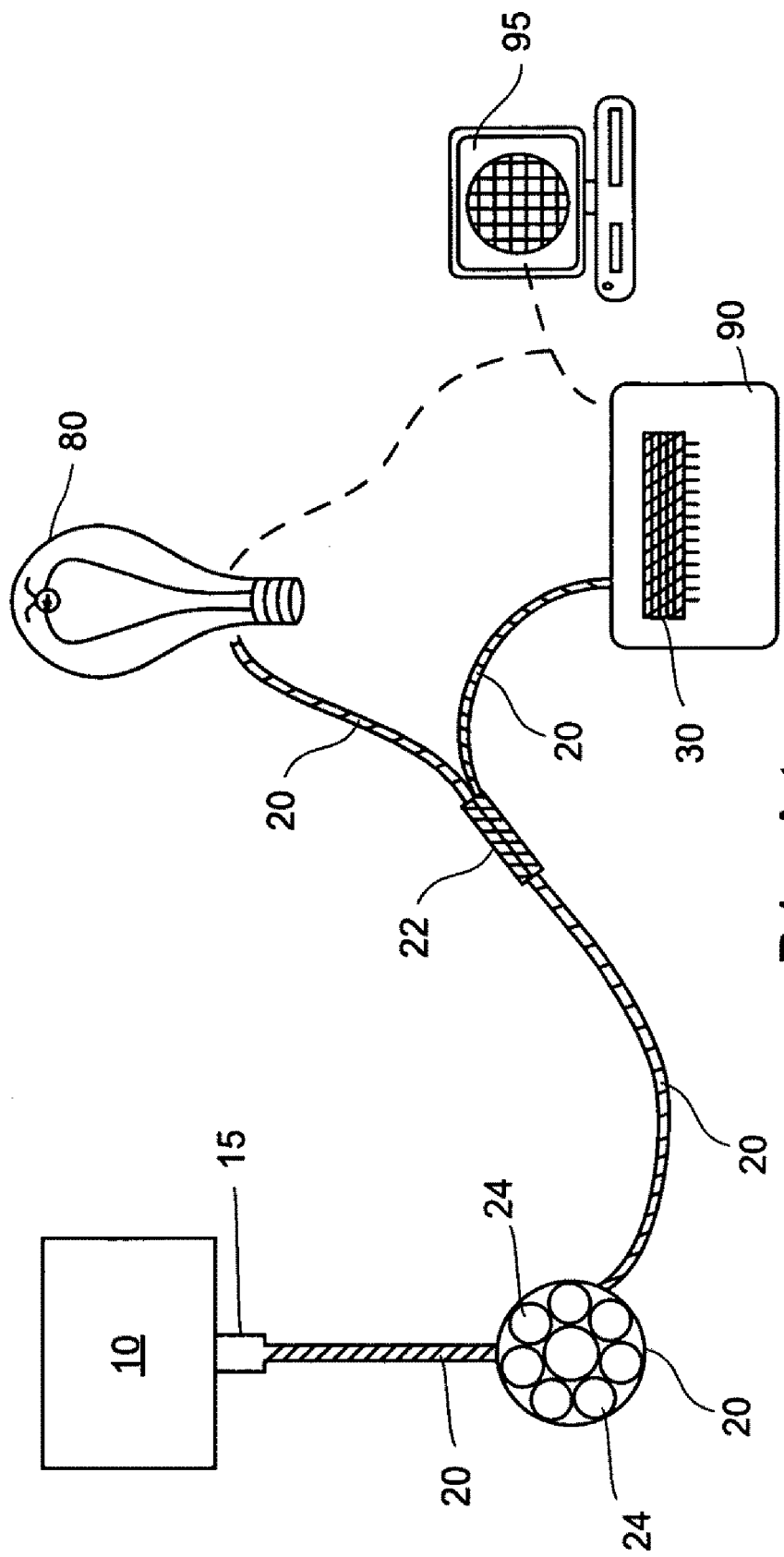
FIG. 1b is a schematic of a monitoring and measurement apparatus.

A typical spectral collection and analysis tool is shown in FIG. 1b. A fiberoptic cable 20, or other transmission medium, is coupled to an environment such as a chamber 10 by a collimator 15, and is capable of collecting light returning from a surface of a wafer being processed, or alternatively collecting light from plasma emissions emanating from the wafer being processed within the chamber 10. The fiberoptic cable 20 passes the received light to a spectrograph 90 (also known as a spectrometer) for analysis. The fiberoptic cable 20 is comprised of at least one fiber 24. In most cases, a plurality of the fiber 24 will be bundled together within the fiberoptic cable 20. The bundle of the fiber 24 within the fiberoptic cable 20 can allow for transmission of the illumination source 80 and collection of signals off the surface of the wafer within the same fiberoptic cable 20. A coupler 21, provides for the fiberoptic cable 20 to be attached to both the illumination source 80 and the spectrograph 90.

The spectrograph 90 may be incorporated in the computer 95, or may be a standalone unit that serves as input into the computer 95. The spectrograph 90 may include a discrete sensing device 30 such as a photo transducer or other charge-coupled device array (CCD array). A CCD array is an arrangement of semiconductor devices that provide electric charge output of one semiconductor device to charge an adjacent one. The discrete sensing devices 30 breaks the received light (signal) into discrete wavelengths. The spectrograph 90 may vary the exposure time, thereby producing a number of samples to be integrated into a single instance or data set.

The illumination element 80 may be comprised of any suitable light source such as a xenon lamp (about 120 nm to about 900 nm) capable of providing broadband wavelengths of light. For plasma diagnostic systems the process performed within the chamber 10 serves as the light source and the illuminating element 80 is not be necessary. In the case of plasma diagnostics, the fiberoptic cable 20 provides transmission of light from the chamber to the spectrograph.

The selection of the illumination element 80 may be dependent on the type of films to be measured by the system used for collecting data from spectral sources. A broad range of dielectric and semi-conductive materials are transmissive at certain wavelengths of light. Transmissive films allow particular wavelengths of light to pass through to lower material layers based on the index of refraction and extinction coefficient of the particular material. Without limitation, example lists of suitable films can be readily obtained from a number of sources. One example source may be *A User's Guide to Ellipsometry*, Harland G., Tompkins, Academic Press, Inc., New York, 1993, pg. 253-255, which is herein incorporated by reference.

If the illumination source 80 is used, material properties of the film on the wafer, such as the refractive index and extinction coefficient of the material, allow certain wavelengths of light to pass through the material and be reflected by lower layers while other wavelengths of light are reflected only off the top surface of that film layer. Interference based on reflected light of multiple wavelengths from a pair of surfaces provides a means of measuring the thickness of materials. Spectral reflectometry provides a technique for determination of the thickness of film layers based on the difference in the optical path length between interfaces. Co-pending U.S. patent application Ser. No. 10/810,209 entitled "METHOD AND APPARATUS FOR MEASUREMENT OF THIN FILMS AND RESIDUES ON SEMICONDUCTOR SUBSTRATES," filed on Mar. 26, 2003 provides for full surface mapping of a rotating wafer through use of optical sensors using reflectometry or inductive sensors and is incorporated by reference, herein.

The illumination element 80 may be continuously illuminated or may be pulsed or flashed at defined periods to enable error subtraction (smoothing or averaging). A computer 95 in concert with a spectrograph 90 (described below) can control operation of the strobe, including parameters such as the period of flashing the illumination element 80. The illumination element 80 may be housed within the system for collecting data from spectral sources.

Other forms of analysis are available for thin films including ellipsometry. Linearly polarized light, provided by an illumination element 80 in via the fiberoptic cable 20, when reflected off a thin film becomes elliptically polarized. Analysis of this change across the spectrum (provided by spectrograph 90 described above) provides properties of the film such as thickness and the refractive index.

In addition to coordinating the various control activities of the spectral analysis system, the computer 95 is capable of generating a film thickness map, or profile of the films on the wafer. The map provides important information for subsequent processing of the wafer. Several embodiments of charts displaying information about the layers on the substrate are described in U.S. patent application Ser. No. 10/331,194, entitled "USER INTERFACE FOR QUANTIFYING WAFER NON-UNIFORMITES AND GRAPHICALLY EXPLORE SIGNIFICANCE", filed on Dec. 24, 2002, and is incorporated by reference herein.

Feedback from the substrate is collected at a determined sample rate; an amount of time including a pulse of the light source, the signal or signals returned from the surface of the substrate and subsequent processing of that signal or signals. A data set may be determined from one or more samples of the acquired signal or signals after a suitable degree of smoothing, averaging or other algorithm is applied. The data set consists of a number or relative strength for each wavelength analyzed.

Figure 2A:
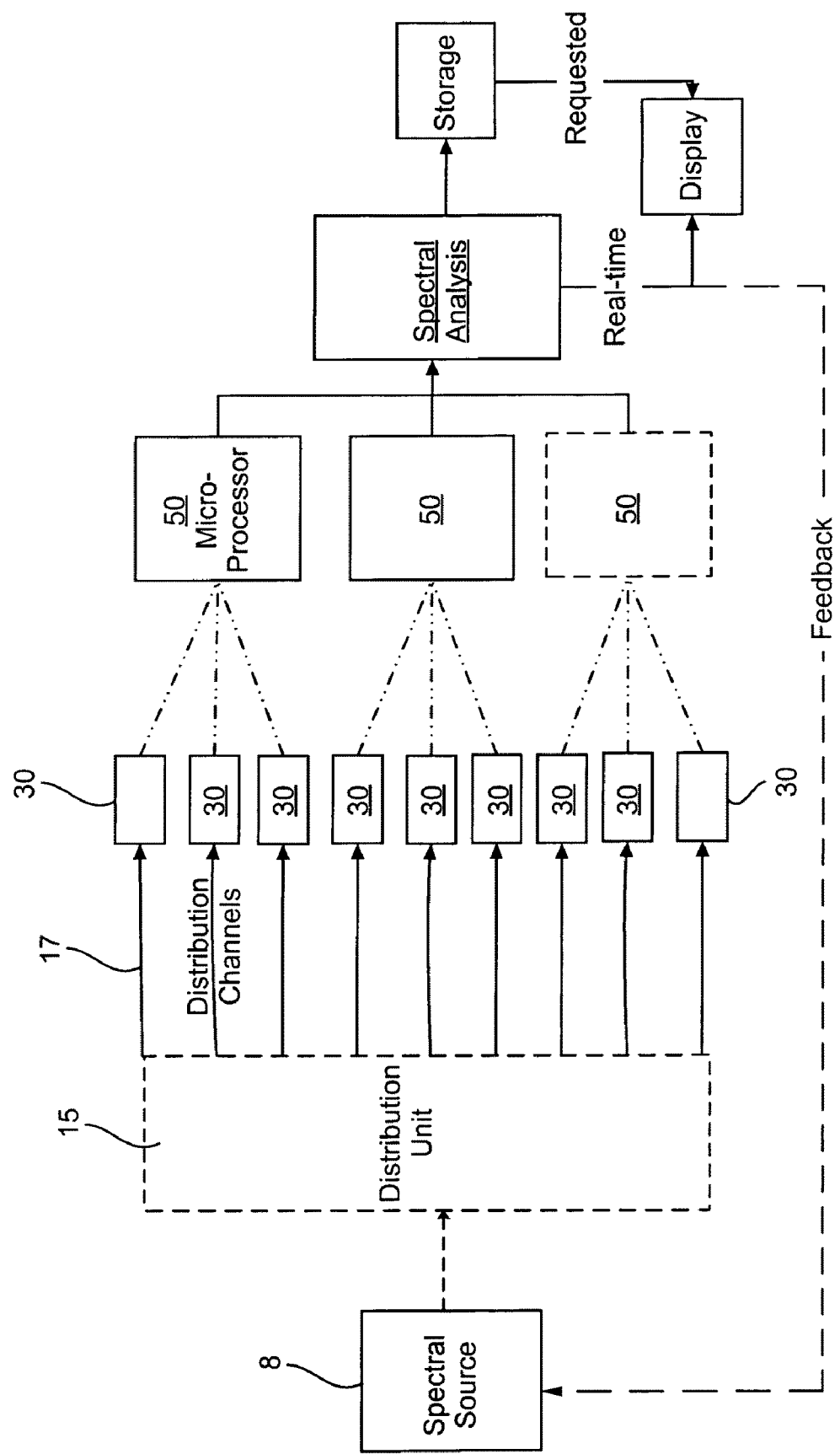
FIG. 2a is an apparatus capable of reducing data processing time in a spectral analysis tool by separating transmission lines, in accordance with one embodiment of the present invention.

FIG. 2a illustrates an apparatus capable of reducing data processing time in a spectral analysis tool by separating distribution channels, in accordance with one embodiment of the present invention. A spectral source 8 such as a process chamber provides a source of light, such as light reflected off a wafer surface or emissions from a plasma. Light from the spectral source 8 is transmitted to a distribution unit 15. The transmission of the light may be accomplished through a suitable communication media such as a fiberoptic cable. The distribution unit 15 is capable of distributing the light from the spectral source 8 into various distribution channels 17. The distribution channels 17 are capable of transmitting the light to discrete sensing devices 30 such as photo transducers or charge-coupled device arrays. The discrete sensing devices 30 are capable of characterizing the light by wavelength or bands of wavelengths. The discrete sensing devices 30 can be tuned so as to register particular bands of wavelengths from the visible electromagnetic spectrum, for instance 300 nm-350 nm, based on the number of pixels dedicated to the particular banding of light. The discrete sensing devices 30 will have to be calibrated or aligned in a way that will allow for subsequent signals to be referenced against a known signal. By splitting the spectrum of light across multiple discrete sensing devices 30, the bands of light can be effectively split producing more accurate and timely characterizations within particular bands. Allowing the discrete sensing devices 30 to be tuned to different wavelength bands also allows for flexibility and more efficient use of processing algorithms. When summed together the bands provide for a complete analysis of the entire spectrum. Output signals from the discrete sensing devices 30 are transmitted to multiple processors 50 capable of classifying, combining ordering and otherwise processing the data obtained from the discrete sensing devices 30. The processors 50 may be processing cores, digital signal processors (DSP), general purpose processors or microprocessors. By implementing multiple processors 50 the reduction and processing of the data is efficiently performed enabling increased sample rates and corresponding data.

Still referring to FIG. 2a, output from the multiple processors 50 provides a complete analysis of the environment within the spectral source 8. The spectral analysis can then be stored or displayed, or both. The spectral analysis can be compared with historical data, or otherwise processed for intermediate or end use. In one embodiment, the spectral analysis provided by the system is displayed in near real-time while being stored or logged in a storage device. The stored information can be requested for display at a later time. The spectral analysis provided by the above described system can also serve as feedback to the spectral source 8. Results of the spectral analysis provide a quantification of the environment within the spectral source 8 such that diagnosis of particular processes may be accomplished. In one embodiment, spectral analysis may diagnose faults or known failures based on a particular emission pattern sensed by the system. In the case of an unexpected emission pattern, feedback from the system may terminate the process within the spectral source 8 or adjust the process to affect a result that is deemed within specified tolerances. Performing as a source of real-time feedback the spectral analysis tool can assist in the manufacturing conformance of electronic devices (integrated circuits, semiconductors, memory and the like).

Figure 2B:
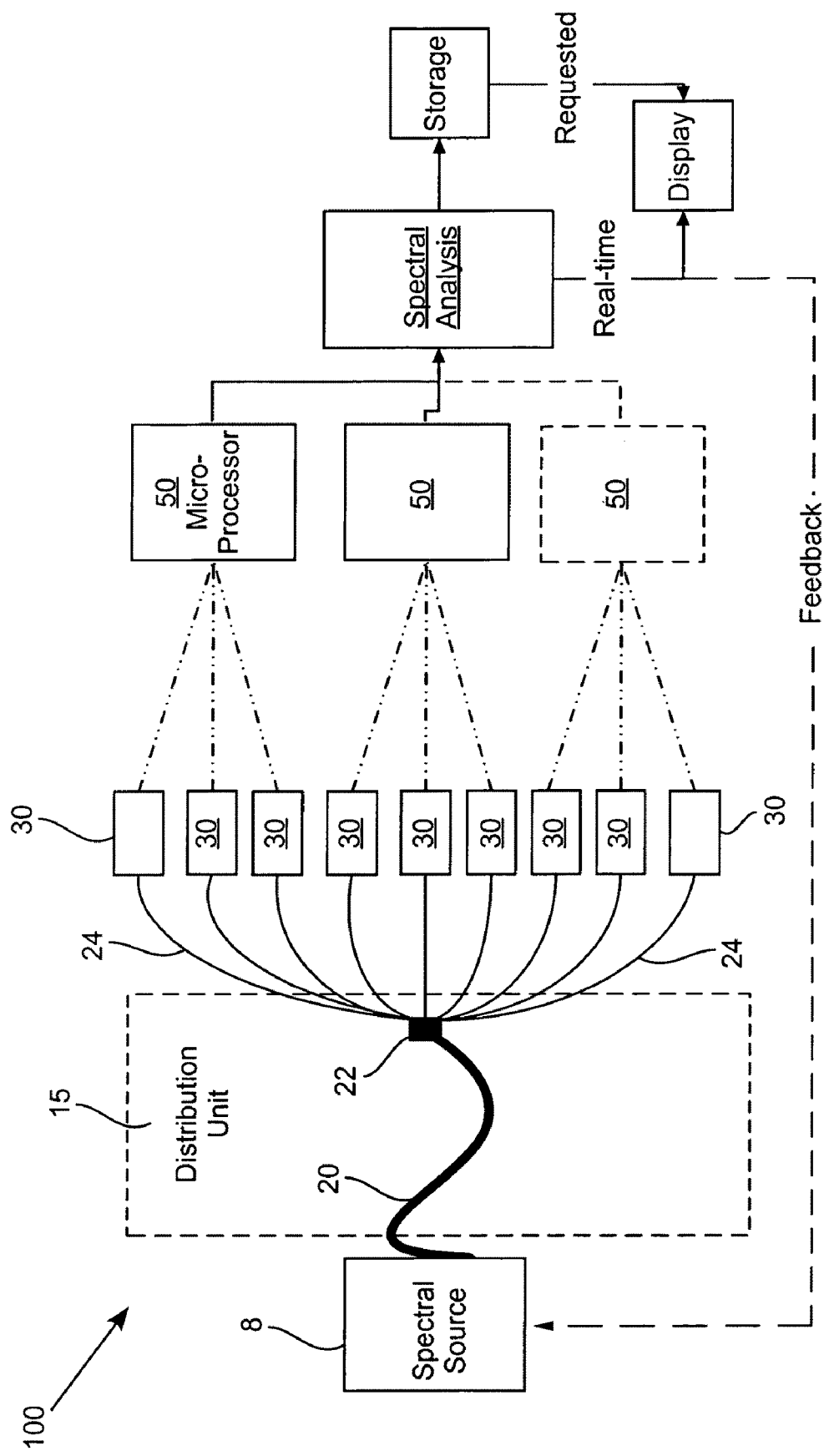
FIG. 2b provides a distribution unit capable of separating light emissions in to distribution channels for processing, in accordance with one embodiment of the present invention.

FIG. 2b provides a particular embodiment of the present invention. As discussed above a fiberoptic cable 20 or other transmission medium, is coupled to the spectral source 8, which may be an etch process chamber or other environment that emits energy in the form of light. The fiberoptic cable 20 is connected to a splitter 22 capable of splitting transmission lines 24 within the fiberoptic cable 20. Light is propagated within the transmission lines 24 to discrete sensing devices 30 such as charge-coupled device arrays. The processing of the signals from the discrete sensing devices 30 is accomplished as discussed above in FIG. 2. Similarly as above, the spectral analysis tool can provide feedback to the spectral source 8 tailoring or terminating the process therein. The difference in this approach is that the full spectrum of light is passed to each discrete sensing device 30.

Figure 3:
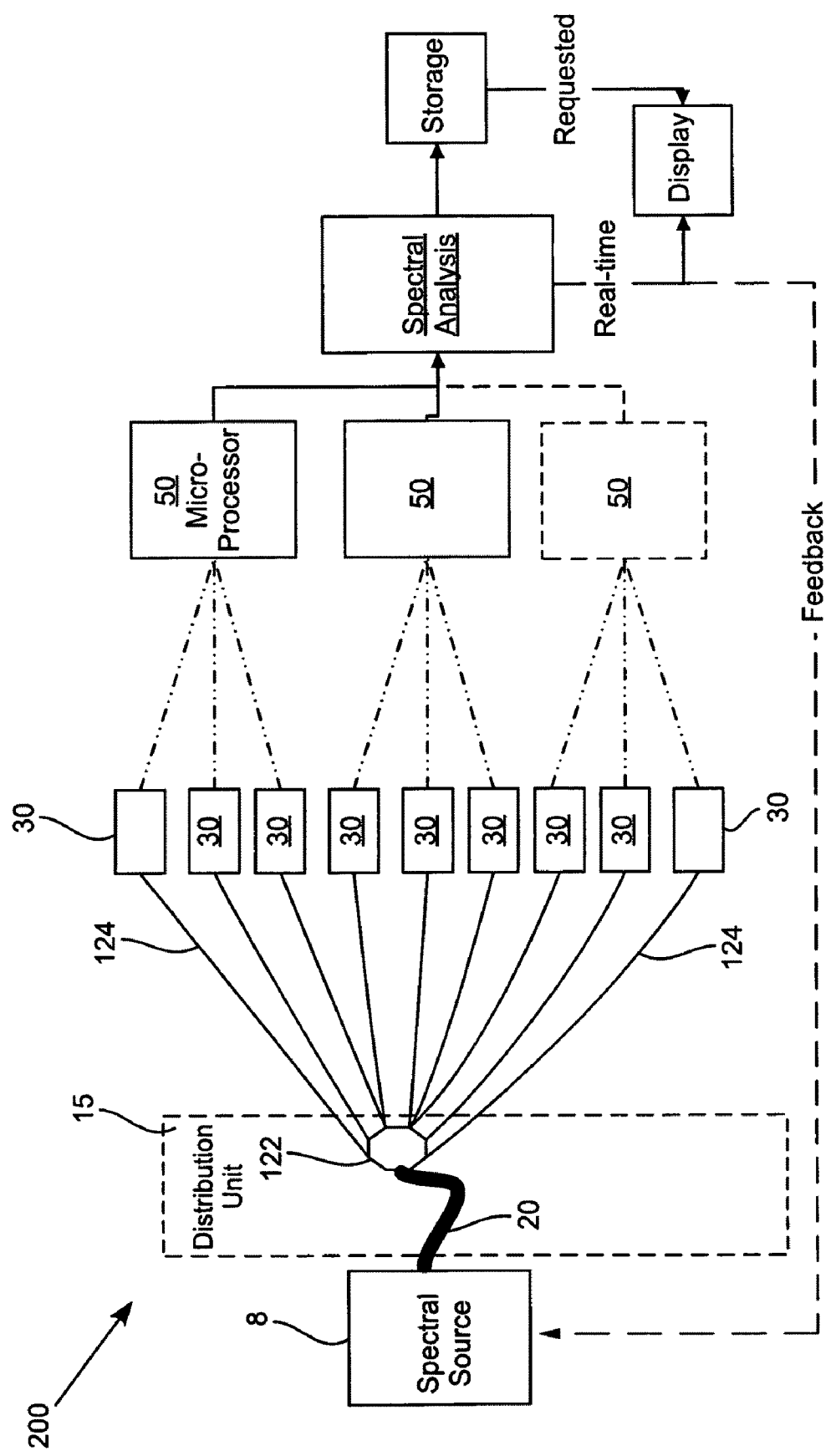
FIG. 3 is an apparatus capable of reducing data processing time in a spectral analysis tool by use of a rotating shutter, in accordance with one embodiment of the present invention.
Figure 4:
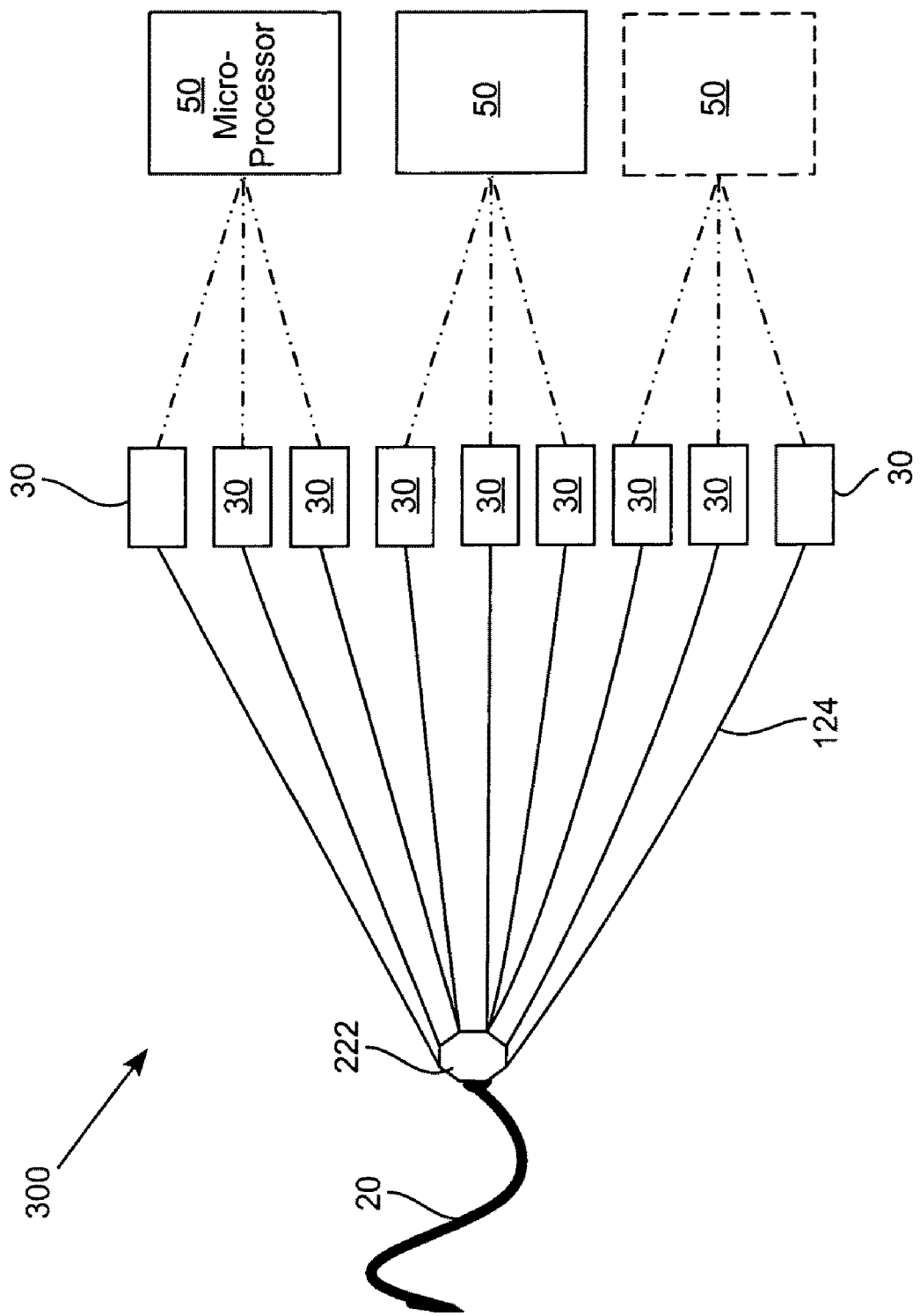
FIG. 4 an apparatus capable of reducing data processing time in a spectral analysis tool by use of a rotating mirror ball, in accordance with one embodiment of the present invention.
Figure 5:
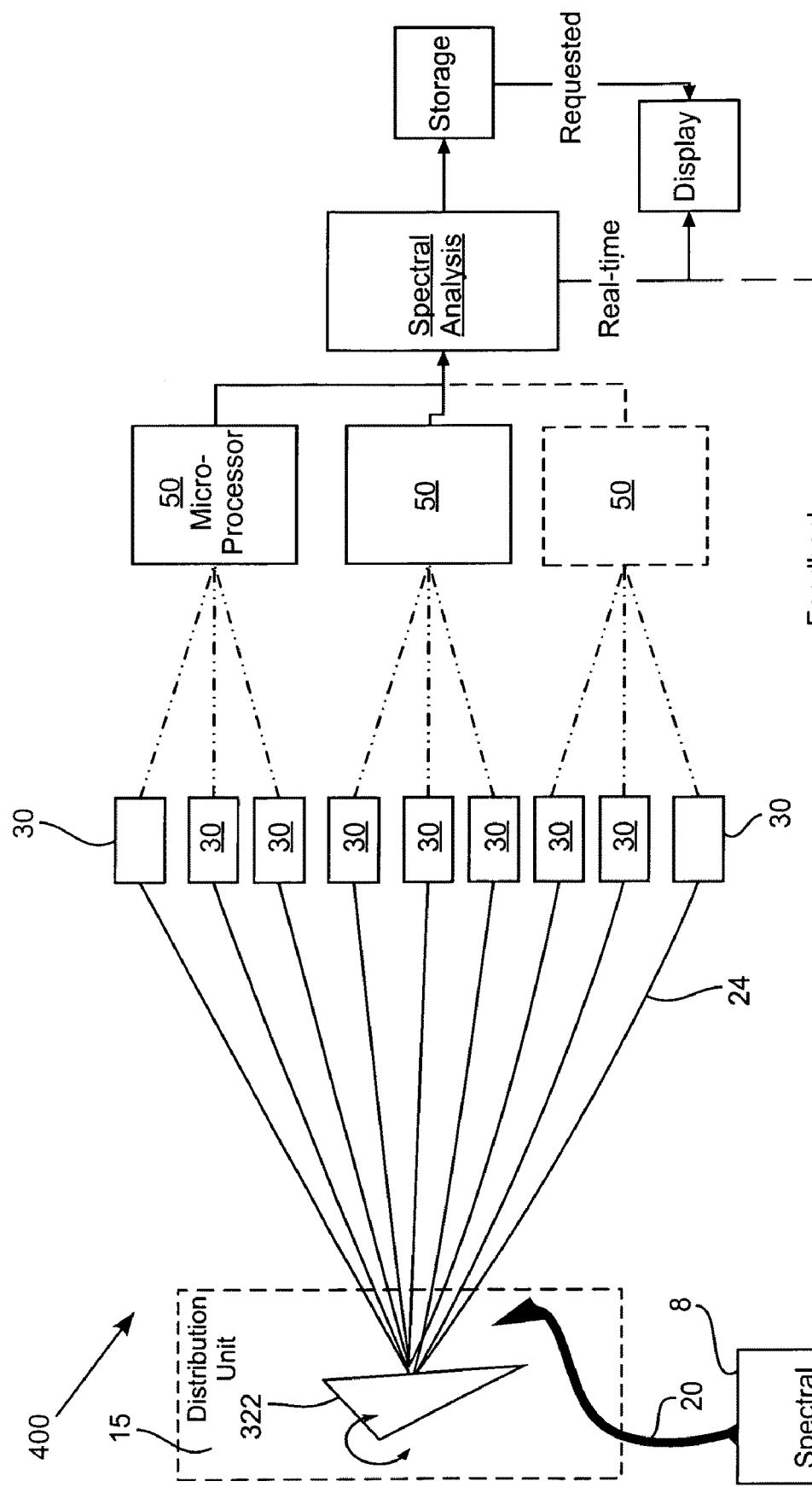
FIG. 5 an apparatus capable of reducing data processing time in a spectral analysis tool by use of a scanning mirror, in accordance with one embodiment of the present invention.
Figure 6:
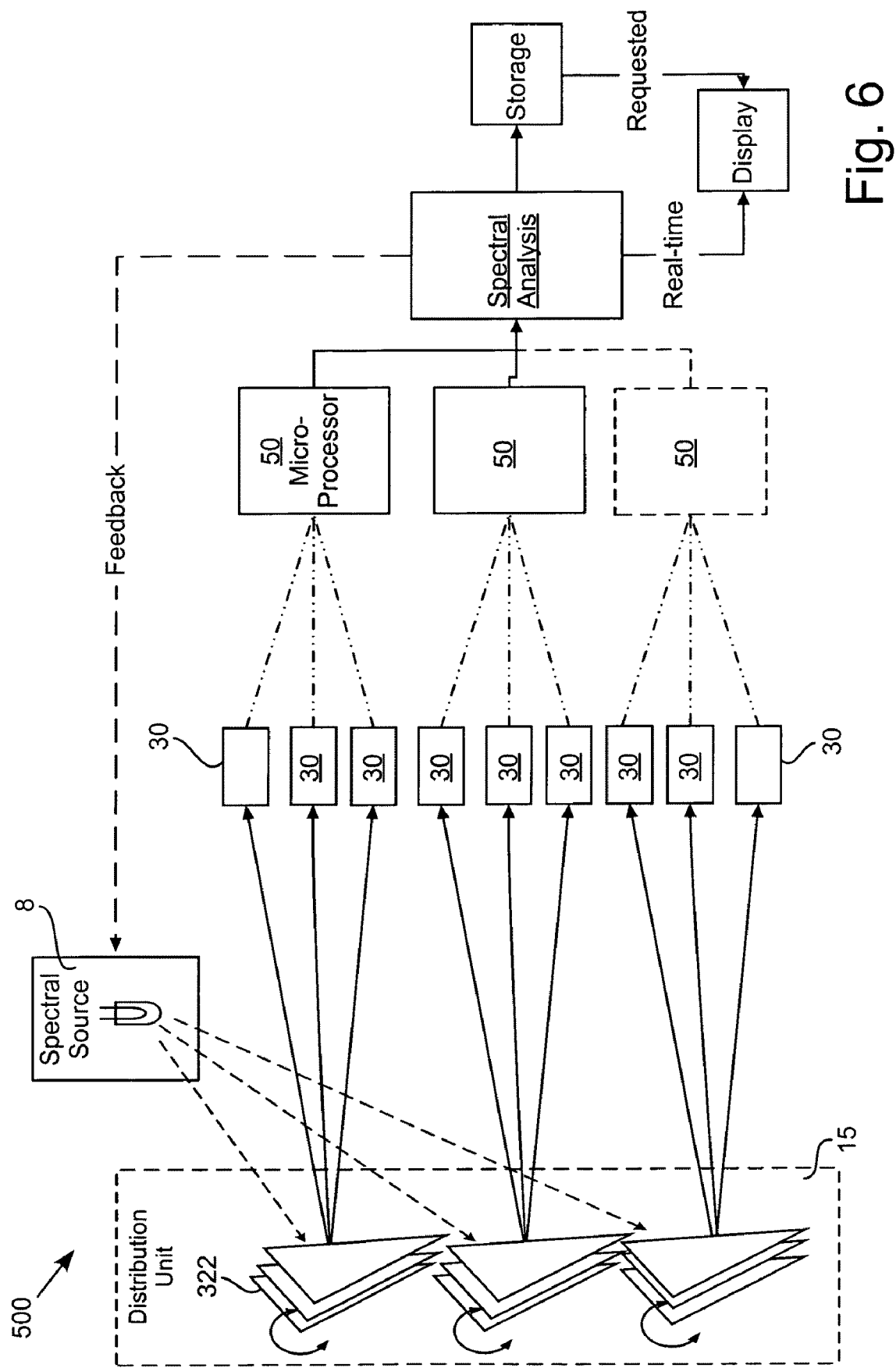
FIG. 6 an apparatus capable of reducing data processing time in a spectral analysis tool by use of a scanning mirror, in accordance with one embodiment of the present invention.

FIGS. 3-6 provide different methods of splitting the signals from the environment or spectral source 8 in order to efficiently process and classify the environment, providing feedback which may be used to terminate or tailor the process. There are several methods of separating the signal into discrete parts. One means for splitting light from environment into a plurality of spectral data units is shown in FIG. 3. A rotating shutter 122 or timed distribution provides a means for distributing the signal from the environment via the fiberoptic cable 20 to the discrete sensing devices 30 which are in communication with the processors 50. Alternatively another means for splitting light from the environment is shown in FIG. 4. A rotating mirror ball 222 or equivalent reflecting surface provides a means of splitting light provided from the environment through a fiber-optic cable 20 and to the discrete sensing devices 30. FIG. 5 illustrates another means for splitting light through the use of a scanning mirror 322 which is capable of reflecting light emitted from the fiber-optic cable 20 on to a series of discrete sensing devices 30 prior to separate processing by the processors 50. In one embodiment, the scanning mirror 322 may be holographic in nature. FIG. 6 provides a series of scanning mirrors 322 capable of scanning light from the environment across a series of discrete sensing devices 30. The scanning mirrors 322 could be part of a larger multi-mirror array such as a micro-electromechanical system (MEMS array) capable of reflecting portions of the light across a series of discrete sensing devices 30.

Figure 7:
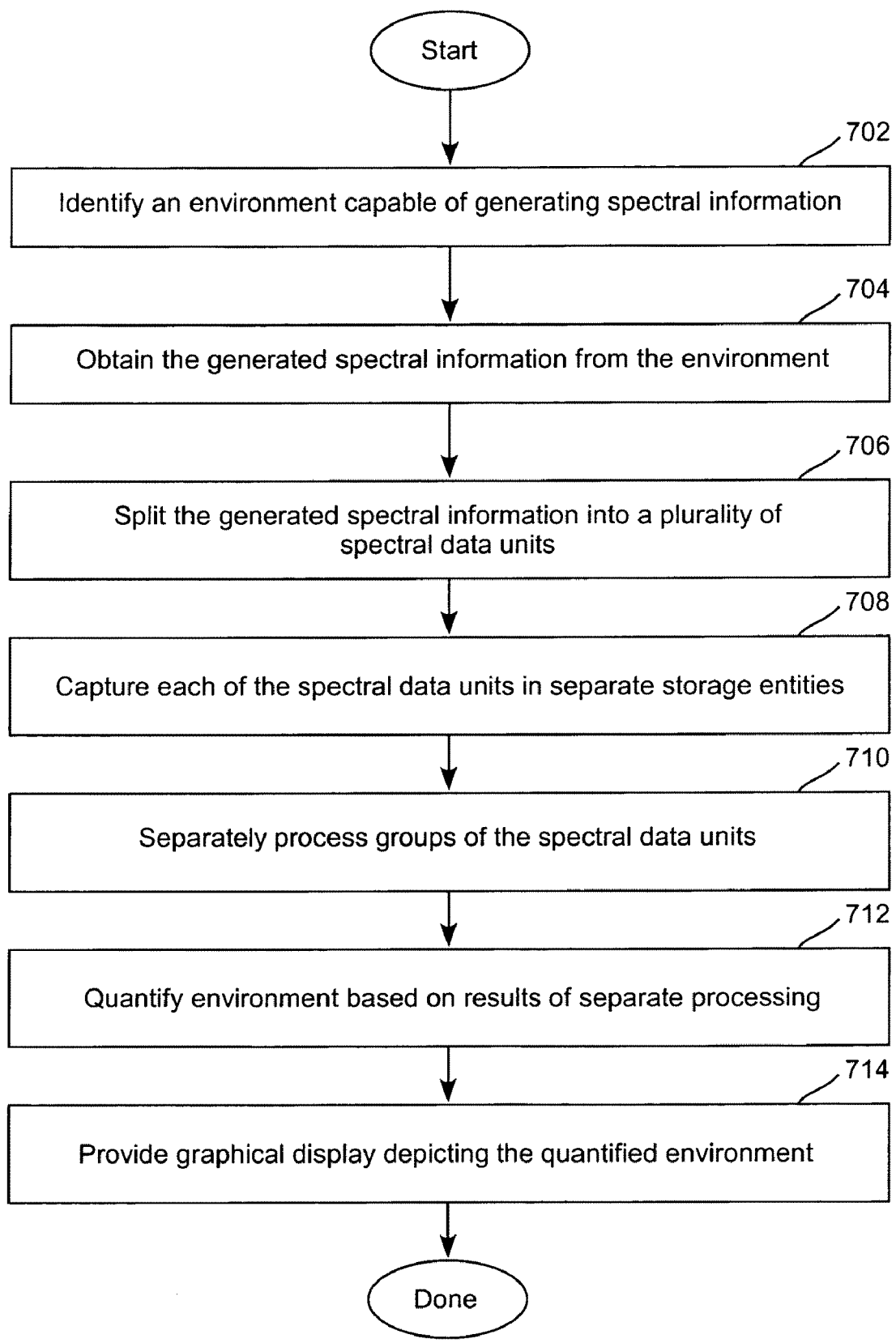
FIG. 7 is a flow chart of a method for reducing data processing time in a spectral analysis tool, in accordance with one embodiment of the present invention.

FIG. 7 is a flow chart that describes a method of processing optical signals. In operation 702, an environment capable of generating spectral information is identified. A reaction chamber capable of processing substrates may be one such environment. In operation 704, spectral information is obtained from the environment by sensors or transmission media adjacent the environment as described in FIGS. 1-6 above. In some wafer processing environments, for example during plasma etch operations, it is possible to capture light reflected off the wafer in order to perform interferometry in addition to capturing light emitted from a plasma discharge located above the wafer. The spectral information obtained is then split into a plurality of spectral data units in operation 706. The spectral data units are bands of wavelengths from the electromagnetic spectrum. Each of the spectral data units are captured in separate storage entities in operation 708. The storage entities are CCD arrays or similarly designed photo transducers capable of storing light signals. In operation 710 the spectral data units are separately processed. The processing of the data is performed by processors such as microprocessors. In operation 712, the separate processing of operation 710 provides a quantification of the environment identified in operation 702. The quantification of the environment may include a description of the chemical species present in the environment or process chamber and information about the materials present on the wafer. The quantification can also be used to assess the progress of the operations performed within the environment or process chamber or note the change or rate of chance of such processes. Synthesized information about the process within the environment can be critical in monitoring and in the limit, correcting or tuning of processes within the environment.

Figure 8A:
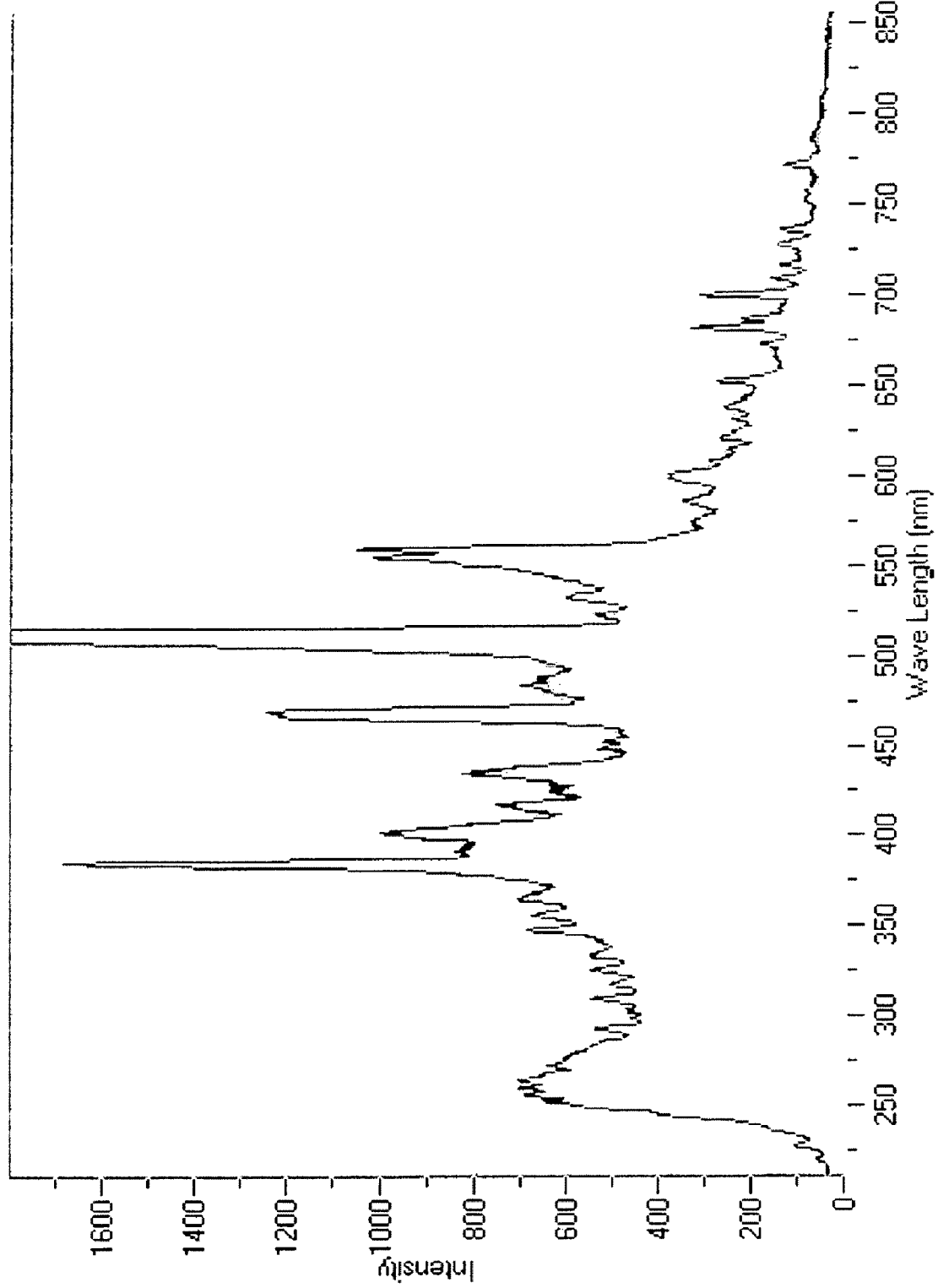
FIG. 8a is a spectral graph displaying intensities of various wavelengths from the environment, in accordance with one embodiment of the present invention.

Information extracted from the environment and processed by the method described above can be displayed in several formats depending on the application or result desired. As shown in FIG. 8a, spectral intensity obtained by the system may be graphically represented by wavelengths across the visual spectrum. Alternatively as shown in FIG. 8b, data obtained from the environment may be represented in a spreadsheet. In FIG. 8b, intensities of particular wavelengths of light are recorded for the duration of the processing. The progression of the processing at particular wavelengths can be further analyzed in order to characterize or control aspects of the processing operation.

Figure 9A:
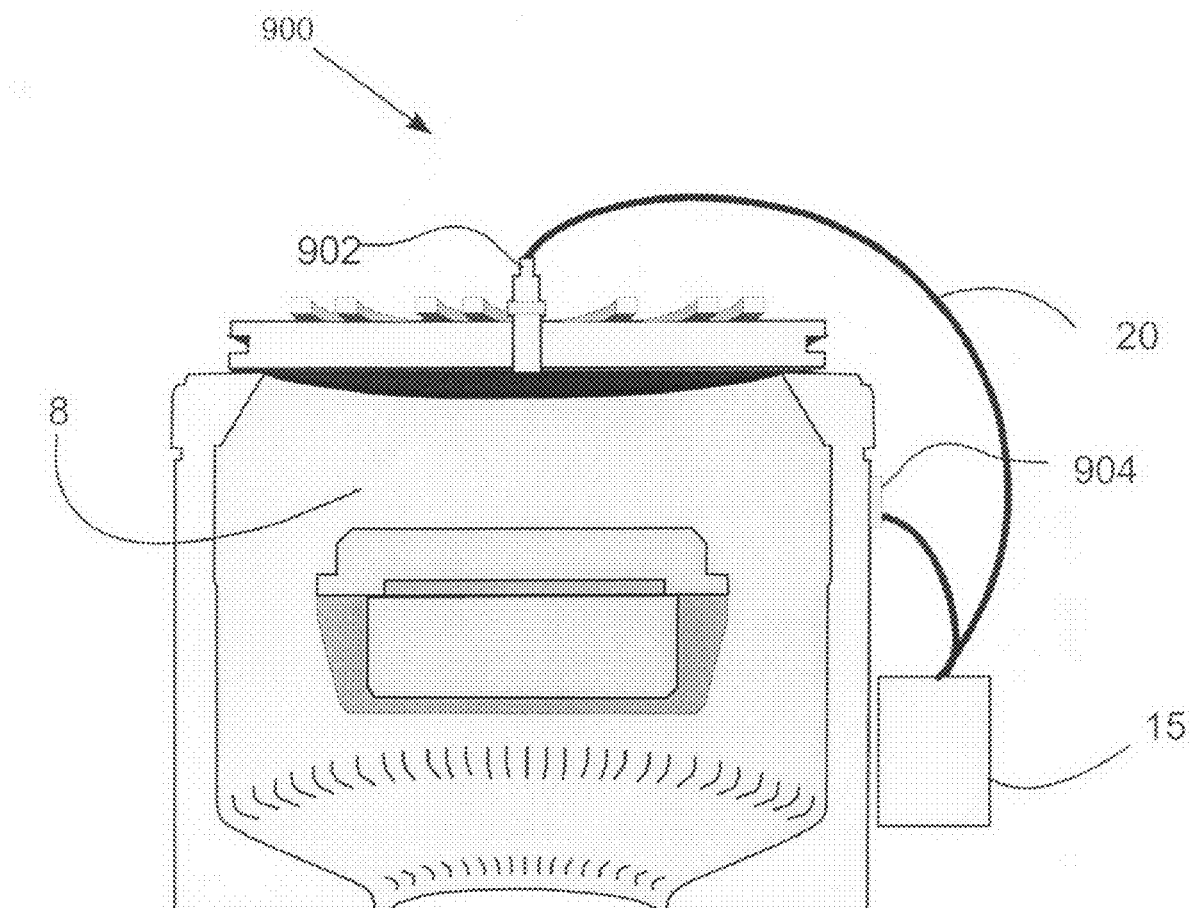
FIG. 9a is cross-sectional view of a process chamber complete with the spectral analysis system in accordance with one embodiment of the present invention.

In another embodiment of the present invention, the system and method for obtaining and processing spectral data is part of a larger processing system, as shown in FIGS. 9a and 9b. The spectral data and analysis performed by the present invention is a component of a processing tool 900 capable of processing semiconductor wafers. The processing tool 900 includes a process chamber, also referred to as a spectral source 8, capable of containing gaseous species, radio frequency (RF) energy, and a material to be etched or deposited. The processing tool 900 could be a single chamber as shown in FIG. 9a, or the processing tool 900 could be one of a plurality of chambers (typically up to 4) clustered together around a transport module 7. The transport module 7 is capable of transporting material into the chambers for processing. The process chamber has ports 902 and 904 adjacent to a location where a reaction may be contained in the chamber, the ports being capable of receiving signals reflected from the material (902) and from plasma emissions above the material (904). The port 904 may be referred to simply as a window or endpoint window, that allows for capturing light emanating from within the process chamber. Examples of a suitable process chambers are described in U.S. Pat. No. 4,948,458, entitled "Method and apparatus for producing magnetically-coupled planar plasma" and U.S. Pat. No. 5,534,751, entitled, "Plasma etching apparatus utilizing plasma confinement." These patents are herein incorporated by reference. The processing tool includes transmission media, such as a fiberoptic cable 20, capable of transmitting the signals from the processing chamber to a distribution unit 15 capable of splitting the signals reflected from the material or received from plasma emissions above the material into a plurality of spectral data units (as described in FIG. 2a above. The processing tool 900 includes storage entities, such as CCD arrays or photo transducers capable of capturing each of the spectral data units, and data processors capable of separately processing groups of the spectral data units. The CCD arrays and the data processors may be housed in a separate enclosure on the processing tool 900 configured to produce a complete processing of the plurality of spectral data units. The processing tool 900 can obtain characteristics of the material in the process chamber and the progress of the processing operations through analysis of information obtained from the signals captured by the system. Information obtained by the monitoring operation can serve as input to ongoing processing operations providing correction or termination of processes as appropriate, based on predetermined program instructions. Coordination and comparison of spectral information with machine parameters can be carried out for advanced process control.

Information obtained by the photo transducer or CCD array and multiple processors described in the present disclosure as well as operation of the various pieces of equipment of the present invention are capable of being controlled by a computer employing the use of program instructions. With the above embodiments in mind, it should be understood that the invention may employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations described herein that form part of the invention are for useful machine operations. The invention also relates to a device or an apparatus for performing these operations. The apparatus may be specially constructed for the required purposes of processing signals obtained by the optical and inductive sensors, or it may be a general-purpose computer selectively activated or configured by a computer program stored in the computer. In particular, various general-purpose machines may be used with computer programs written in accordance with the teachings herein, or it may be more convenient to construct a more specialized apparatus to perform the required operations.

One embodiment of the present invention can also be embodied as computer readable code on a computer readable medium. The computer readable medium is any data storage device that can store data which can be thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over network coupled computer systems so that the computer readable code is stored and executed in a distributed fashion.

In summary, the embodiments of the present invention provide for efficient collection and classification of spectral data through the use of multiple device arrays and split processing. The invention has been described herein in terms of several exemplary embodiments. Other embodiments of the invention will be apparent to those skilled in the art from consideration of the specification and practice of the invention. The embodiments and preferred features described above should be considered exemplary, with the invention being defined by the appended claims.

What is claimed is:

1. A method for obtaining data from a spectral source, comprising:

identifying an environment that is capable of generating spectral information;

obtaining the generated spectral information from the environment from one location of the environment;

for the spectral information obtained from the one location, splitting the generated spectral information into a plurality of spectral data units that are tuned to register particular bands of wavelengths from a visible electromagnetic spectrum, wherein the splitting the generated spectral information includes rotating a shutter to enable capturing the particular bands of wavelengths for each of the spectral data units;

capturing the particular bands of wavelengths for each of the spectral data units in separate storage entities;

separately and in parallel processing each of the particular bands of wavelengths of the plurality of spectral data units; and combining an output of the processing to produce a complete processing of the particular bands of wavelengths of the plurality of spectral data units, the complete processing defining a quantification of the environment from the one location.

2. The method of claim 1, wherein the environment is a chamber that includes one or both of spectra reflected off the surface of a substrate and emissions generated from a plasma.

3. The method of claim 1, wherein a transmission media assists in obtaining the generated spectral information.

4. The method of claim 1, wherein the capturing further comprises,
storing a defined number of pixels for the separate storage entities.

5. The method of claim 1, wherein the defined number of pixels are assigned to correspond to the particular bands of wavelengths.

6. The method of claim 1, wherein tuning to register particular bands of wavelengths includes,
filtering selected wavelength ranges.

7. A method for obtaining data from a spectral source, comprising:
identifying an environment that is capable of generating spectral information;
obtaining the generated spectral information from the environment from one location of the environment;
for the spectral information obtained from the one location, splitting the generated spectral information into a plurality of spectral data units that are tuned to register particular bands of wavelengths from a visible electromagnetic spectrum, wherein the splitting the generated spectral information includes, rotating a mirror ball to enable capturing the particular bands of wavelengths for each of the spectral data units;
capturing the particular bands of wavelengths for each of the spectral data units in separate storage entities;
separately and in parallel processing each of the particular bands of wavelengths of the plurality of spectral data units; and
combining an output of the processing to produce a complete processing of the particular bands of wavelengths of the plurality of spectral data units, the complete processing defining a quantification of the environment from the one location.

8. A method for obtaining data from a spectral source, comprising:
identifying an environment that is capable of generating spectral information;
obtaining the generated spectral information from the environment from one location of the environment;
for the spectral information obtained from the one location, splitting the generated spectral information into a plurality of spectral data units that are tuned to register particular bands of wavelengths from a visible electromagnetic spectrum, wherein the splitting the generated spectral information includes, scanning a mirror to enable capturing the particular bands of wavelengths for each of the spectral data units;
capturing the particular bands of wavelengths for each of the spectral data units in separate storage entities;
separately and in parallel processing each of the particular bands of wavelengths of the plurality of spectral data units; and
combining an output of the processing to produce a complete processing of the particular bands of wavelengths of the plurality of spectral data units, the complete processing defining a Quantification of the environment from the one location.

9. The method of claim 1, wherein quantification of the environment includes identification of historical data for comparison and feedback to the environment.

10. The method of claim 1, wherein separately and in parallel processing groups of the particular bands of wavelengths provides for increased processing efficiencies.

11. The method of claim 1, wherein the quantification of the environment includes spectroscopy of reflections, transmissions, and emissions than can emanate from the environment.

12. The method of claim 11, wherein the quantification of the environment is graphically depicted.

13. A method for obtaining data from a spectral source and providing analysis of the obtained data, comprising:
identifying an environment chamber that is capable of generating spectral information from plasma processing;
obtaining the generated spectral information from the environment chamber from one location of the environment chamber during plasma processing;
splitting the generated spectral information into a plurality of spectral data units that are tuned to include only particular bands of wavelengths from a visible electromagnetic spectrum, the generated spectral information obtained from the one location of the environment chamber;
capturing the particular bands of wavelengths for each of the spectral data units in separate storage entities;
storing the a defined number of pixels for the captured particular bands of wavelengths in the separate storage entities;
separately and in parallel processing each one of the particular bands of wavelengths of the plurality of spectral data units; and
combining the separately processed particular bands of wavelengths to produce a complete processing of the particular bands of wavelengths of the plurality of spectral data units, the complete processing defining a quantification of the environment chamber from the one location during the plasma processing;
wherein the splitting the generated spectral information includes rotating a shutter, rotating a minor ball, moving a reflective surface, or scanning a mirror to enable capturing the particular bands of wavelengths for each of the spectral data units.

14. The method of claim 13, wherein obtaining the generated spectral information further comprising:
capturing spectra reflected off the surface of a substrate and emissions generated from a plasma.

15. The method of claim 13, wherein the defined number of pixels are assigned to correspond to the particular bands of wavelengths.

16. The method of claim 13, wherein tuning to register particular bands of wavelengths includes,
filtering selected wavelength ranges.

17. The method of claim 13, further comprising:
generating feedback to the environment chamber in response to analysis of the quantification.

* * * * *